United States Patent
Roux et al.

(10) Patent No.: US 11,510,862 B2
(45) Date of Patent: Nov. 29, 2022

(54) OIL-IN-WATER EMULSION AND COSMETIC USE THEREOF

(71) Applicant: L'OREAL, Paris (FR)

(72) Inventors: Sabine Roux, Chevilly la Rue (FR); Elena Catalan-Martin, Chevilly la Rue (FR); Chloé Laidboeur, Chevilly la Rue (FR)

(73) Assignee: L'OREAL, Paris (FR)

( * ) Notice: Subject to any disclaimer, the term of this patent is extended or adjusted under 35 U.S.C. 154(b) by 31 days.

(21) Appl. No.: 16/471,747

(22) PCT Filed: Dec. 21, 2017

(86) PCT No.: PCT/EP2017/084249
§ 371 (c)(1),
(2) Date: Jun. 20, 2019

(87) PCT Pub. No.: WO2018/115373
PCT Pub. Date: Jun. 28, 2018

(65) Prior Publication Data
US 2020/0022899 A1     Jan. 23, 2020

(30) Foreign Application Priority Data
Dec. 22, 2016 (FR) ..................... 1663196

(51) Int. Cl.
*A61K 8/36*   (2006.01)
*A61K 8/81*   (2006.01)
*A61K 8/06*   (2006.01)
*A61K 8/34*   (2006.01)
*A61K 8/92*   (2006.01)
*A61Q 19/00*  (2006.01)

(52) U.S. Cl.
CPC ............ *A61K 8/8158* (2013.01); *A61K 8/062* (2013.01); *A61K 8/345* (2013.01); *A61K 8/36* (2013.01); *A61K 8/922* (2013.01); *A61Q 19/007* (2013.01)

(58) Field of Classification Search
CPC ...... A61K 8/8158; A61K 8/062; A61K 8/345; A61K 8/36; A61K 8/922; A61K 8/342; A61K 8/37; A61K 8/39; A61Q 19/007
See application file for complete search history.

(56) References Cited

U.S. PATENT DOCUMENTS 10,363,212 B2    7/2019  Charton et al.
2015/0352016 A1* 12/2015 Shah ................ A61K 8/4993
                                                        424/59

FOREIGN PATENT DOCUMENTS

| EP | 3 269 426 A1 | 7/2018 | |
| FR | 3 021 531 A1 | 12/2015 | |
| FR | 3021528 A1 * | 12/2015 | ............ A61K 8/927 |
| JP | 2015 218163 A | 12/2015 | |
| WO | WO-2013057118 A2 * | 4/2013 | ............ A61Q 19/08 |
| WO | WO 2016/046358 A1 | 3/2016 | |

OTHER PUBLICATIONS

Woodruff, Emulsifiers & Surfactant, 2015, SPC, pp. 1-7. (Year: 2015).*
Ikeda (www.ikedabussan.com/itemindex/itemdetail/234, last accessed Jul. 8, 2021) (Year: 2021).*
Paula Lennon, "NewSkincare, Suncare and Make-Up Formulations Containing Emulium Mellifera", IP.Com Journal, Nov. 25, 2014.
P Lennon, "Cosmetic Formulations Containing Emulium Mellifera", IP.Com Journal, Jan. 8, 2014.
Opposition dated Jul. 1, 2021 to EP 3558231 B1 / Application No. EP 17821919.2.
Extract from the Mintel database; Record ID: 3491073; Mild Cleansing Emulsion; Oct. 2015.
Extract from the Mintel database; Record ID: 4293409; Radiance Cream; Sep. 2016.
Extract from the Mintel database; Record ID: 3552881; Moistening Cream; Nov. 2015.
"Wachse—eine unverzichtbare Stoffklasse" [Waxes—a vital class of compound]; published in Kosmetik International 2014 (10), pp. 52-56.
Technical Data Sheet for Emulium Mellifera™, Jul. 16, 2015.
Technical Data Sheet for Acticire™ MB; Dec. 21, 2016.

* cited by examiner

*Primary Examiner* — Ali Soroush
(74) *Attorney, Agent, or Firm* — Polsinelli PC

(57) ABSTRACT

The invention relates to a composition of oil-in-water emulsion type comprising: —at least one polyol in a content ranging from 7% to 25% by weight relative to the total weight of the composition; —water in a content ranging from 60% to 90% by weight relative to the total weight of the composition; —at least two nonionic surfactants that are different from each other, chosen from a nonionic surfactant of ester type comprising a mixture of at least one unsaturated ester and of at least one diester of polyglycerol and a nonionic surfactant which is a fatty alcohol with a saturated, linear carbon-based chain containing from 14 to 26 carbon atoms; —at least one wax; —and the mass ratio [total amount of said nonionic surfactant(s) of ester type]/[total amount of said wax] ranges from 0.8 to 2, preferably from 1 to 1.5.

20 Claims, No Drawings

OIL-IN-WATER EMULSION AND COSMETIC USE THEREOF

CROSS REFERENCE TO RELATED APPLICATIONS

This application is a National Phase filing under 35 U.S.C. § 371 of PCT/EP2017/084249 filed on 21 Dec. 2017; which application in turn claims priority to Application No. 1663196 filed in France on 22 Dec. 2016. The entire contents of each application are hereby incorporated by reference.

The present invention relates to a composition for topical application in the form of an oil-in-water (O/W) emulsion, and to the non-therapeutic cosmetic use of said composition for caring for, the hygiene of, protecting and/or making up keratin materials such as bodily or facial skin, in particular for moisturizing said keratin materials.

The skin, which is a protective and exchange barrier with the environment, is both strong and fragile, it may lose its suppleness and its capacity to retain water decreases, then causing skin dryness.

It is known that the stratum corneum or corneal layer, which is the outermost region of the epidermis, is most particularly involved in moisturizing the skin. Located at the interface with the external environment, its function is especially to delay excessive water loss arising from the deeper layers of the epidermis. The stratum corneum also protects against mechanical attack. It also constitutes the first line of defence against UV radiation.

With a thickness of 10 μm, it is composed of vertically stacked corneocytes surrounded by a matrix of lipid-enriched membranes. Thus, it is a two-compartment system that may be compared to a wall of bricks, composed of anuclear cells (the "bricks") and of intercellular lamellar membranes (the "cement"). By virtue of this compact stratified structure, the stratum corneum performs its barrier function by opposing transcutaneous water loss (or TEWL: transepidermal water loss) and by limiting it. It thus efficiently contributes towards the moisturization of the skin via its capacity to take up and retain water, which is mainly located in the intercellular spaces.

For obvious reasons, it is important to ensure a sufficient level of skin moisturization in order to preserve its suppleness, softness, tonicity and/or appearance, and to prevent skin dryness.

It may moreover be necessary to be able to maintain good moisturization over time, and especially when the environmental temperature and/or humidity conditions are variable (cold/hot-hot/cold changes in the course of the day, for example).

In general, a decrease in this level of moisturization may be prevented or treated by treating the stratum corneum with active agents known as moisturizers, for instance glycerol, or with galenical products that can slow down the TEWL, such as reverse emulsions containing mineral oils and derivatives (W/O) via the deposition of a continuous fatty phase that is sufficiently occlusive to maintain the level of moisturization of the stratum corneum.

However, drawbacks are observed with active agents or galenical products of these types. For example, glycerol has the drawback of making formulations tacky, especially when it is used in high concentration.

Galenical products of reverse emulsion (W/O) type generally have an occlusive nature that gives a greasy and tacky finish.

There is thus still a need to find a technical solution for obtaining galenical products that can improve and/or maintain the moisturization of keratin materials such as the skin, especially under variable environmental conditions such as temperature and/or humidity conditions that are variable in the course of the day (for example being adapted to a temperature of 20° C. with 40% relative humidity (RH) or to a temperature of 30° C. with 70% RH), and which at the same time have good cosmetic properties such as a less tacky and less greasy feel and/or little occlusive nature.

The inventors have found, unexpectedly, that compositions in oil-in-water emulsion form, which are the subject of the present invention, make it possible especially to provide, while at the same time having a moisturizing effect, especially throughout the day, compositions that have little occlusive nature and/or that remain pleasant for the consumer, i.e. being sparingly tacky, having a pleasant feel (such as a less greasy feel), and/or having no discomfort sensations such as tautness.

Surprisingly, the compositions according to the invention in oil-in-water emulsion form especially have good film-forming properties, with good resistance of the film formed on keratin materials such as the skin, allowing protection against variable environmental temperature and humidity conditions, while at the same time conserving good cosmetic properties in particular as regards the sensory properties and the comfort of use, minimizing the greasy or tacky feel on application.

The compositions according to the invention especially have good film-forming properties, with a film which remains thin and homogeneous (for instance less than 50 μm) and/or good resistance of the film formed on keratin materials such as the skin, i.e. having good persistence over time, especially over a period of greater than or equal to 3 hours, preferably throughout the day, especially at least 8-10 hours, and/or having good resistance to water and/or to external stresses such as raising of the temperature or the humidity level of the ambient air (especially temperature ranging from 4° C. to 40° C. and humidity ranging from 40 RH to 70 RH).

The compositions according to the invention also allow good moisturization, especially long-lasting moisturization, of keratin materials such as the skin, and/or can improve the biomechanical properties of said keratin materials, such as improved elasticity of the skin.

Thus, one subject of the present invention is a composition of oil-in-water type, preferably a cosmetic composition, comprising:
  at least one polyol in a content ranging from 7% to 25% by weight relative to the total weight of the composition;
  water in a content ranging from 60% to 90% by weight, preferably from 65% to 90% by weight, relative to the total weight of the composition;
  at least two nonionic surfactants that are different from each other, chosen from a nonionic surfactant of ester type comprising a mixture of at least one unsaturated, preferably monounsaturated, ester and of at least one diester of polyglycerol and a nonionic surfactant which is a fatty alcohol with a saturated, linear carbon-based chain containing from 14 to 26 carbon atoms;
  at least one wax,
  and the mass ratio [total amount of said nonionic surfactant(s) of ester type]/[total amount of said wax] ranges from 0.8 to 2, preferably from 1 to 1.5.

In the following text, the expression "at least one" is equivalent to "one or more" and, unless otherwise indicated, the limits of a range of values are included in that range.

Reference will generally be made in the description to weight percentages of active material of the various ingredients or compounds relative to the total weight of said composition.

In one particular embodiment, the composition according to the invention comprises one or more aliphatic monoalcohols comprising from 1 to 6 carbon atoms in a content of less than or equal to 5% by weight relative to the total weight of the composition, in particular in a content of less than or equal to 1% by weight, preferably in a content of less than or equal to 0.50% by weight, and in particular 0 to 0.50% by weight relative to the total weight of the composition.

The term "aliphatic monoalcohol" means any linear or branched, saturated alkane compound bearing only one hydroxyl (OH) function.

The aliphatic monoalcohol(s) present may be chosen especially from ethanol, propanol, butanol, isopropanol and isobutanol, or mixtures thereof.

In one particular embodiment, the composition according to the invention comprises fillers in a content of less than or equal to 5% by weight relative to the total weight of the composition, in particular in a content of less than or equal to 1% by weight, preferably in a content of less than or equal to 0.50% by weight.

The fillers may be chosen from those that are well known to a person skilled in the art and that are commonly used in cosmetic compositions. The fillers may be mineral or organic, and lamellar or spherical. Mention may be made of talc, mica, silica, kaolin, polyamide powders, for instance the Nylon® sold under the name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms and in particular from 12 to 18 carbon atoms, for example zinc, magnesium or lithium stearate, zinc laurate and magnesium myristate.

It is also possible to use a compound that is capable of swelling on heating, and especially heat-expandable particles such as non-expanded microspheres of vinylidene chloride/acrylonitrile/methyl methacrylate copolymer or of acrylonitrile homopolymer or copolymer, for instance those sold, respectively, under the references Expancel® 820 DU 40 and Expancel® 007WU by the company Akzo Nobel.

In one particular embodiment, the composition according to the invention comprises silicone oils in a content of less than or equal to 5% by weight relative to the total weight of the composition, in particular in a content of less than or equal to 1% by weight, preferably in a content of less than or equal to 0.50% by weight.

In one particular embodiment, the composition according to the invention comprises organopolysiloxane elastomers in a content of less than or equal to 5% by weight relative to the total weight of the composition, in particular in a content of less than or equal to 1% by weight, preferably in a content of less than or equal to 0.50% by weight.

As examples of silicone oils, mention may be made, for example, of linear organopolysiloxanes such as dimethylpolysiloxane, methylphenylpolysiloxane, methylhydrogenopolysiloxane and the like; cyclic organopolysiloxanes such as octamethylcyclotetrasiloxane, decamethylcyclopentasiloxane, dodecamethylcyclohexasiloxane and the like; and mixtures thereof.

The polydialkylsiloxanes may be chosen from polydimethylsiloxanes comprising trimethylsilyl end groups, and polydimethylsiloxanes comprising dimethylsilanol end groups, known under the name dimethiconol (CTFA), and preferably polydimethylsiloxanes comprising trimethylsilyl end groups.

The polydialkylsiloxane chosen may be a mixture of dimethicone and dimethiconol (INCI name) available under the trade name Xiameter PMX-1503 FLUID® by the company Dow Corning.

These silicone oils may also be organomodified, such as silicone oils as defined above comprising in their structure one or more organofunctional groups linked via a hydrocarbon-based group.

The organopolysiloxanes are defined in greater detail in Walter Noll's Chemistry and Technology of Silicones (1968), Academic Press. They may be volatile or non-volatile.

Volatile or non-volatile silicone oils, such as volatile or non-volatile polydimethylsiloxanes (PDMS) containing a linear or cyclic silicone chain, which are liquid or pasty at room temperature, in particular cyclopolydimethylsiloxanes (cyclomethicones) such as cyclohexasiloxane; polydimethylsiloxanes containing oxyethylene, alkyl, alkoxy or phenyl groups that are pendent or at the end of the silicone chain, said groups containing from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenyl ethyl trimethylsiloxysilicates and polymethylphenylsiloxanes, may be used.

The term "non-volatile silicone oil" means a silicone oil that remains on the skin or the keratin fibre at room temperature and atmospheric pressure for at least several hours. These oils have in particular a vapour pressure of less than $10^{-3}$ mmHg (0.13 Pa).

As examples of volatile silicone oils that may be used in the invention, mention may be made of:
  volatile linear or cyclic silicone oils, in particular those with a viscosity ≤8 centistokes ($8\times10^{-6}$ m$^2$/s) and in particular containing from 2 to 7 silicon atoms, these silicones optionally comprising alkyl or alkoxy groups containing from 1 to 10 carbon atoms. As volatile silicone oils that may be used in the invention, mention may especially be made of octamethylcyclotetrasiloxane, decamethylcyclopentasiloxane or cyclopentasiloxane, dodecamethylcyclohexasiloxane or cyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane. Cyclohexasiloxane, or dodecamethylcyclohexasiloxane, is especially available under the trade name Xiameter PMX-0246 Cyclohexasiloxane® from the company Dow Corning.

Cyclopentasiloxane, or decamethylcyclopentasiloxane, is especially available under the trade name Xiameter PMX-0245 Cyclopentasiloxane® from the company Dow Corning.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has limited stretchability and contractibility. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, in particular in the presence (C) of a platinum catalyst, as described, for instance, in application EP-A-295 886.

In particular, the organopolysiloxane elastomer may be obtained by reaction of dimethylpolysiloxane bearing dimethylvinylsiloxy end groups and of methylhydrogenopolysiloxane bearing trimethylsiloxy end groups, in the presence of a platinum catalyst.

Compound (A) is the base reagent for the formation of elastomeric organopolysiloxane, and the crosslinking is performed by addition reaction of compound (A) with compound (B) in the presence of catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from trimethylsiloxy-terminated methylhydrogenopolysiloxanes, trimethylsiloxy-terminated dimethylsiloxane/methylhydrogenosiloxane copolymers, and dimethylsiloxane/methylhydrogenosiloxane cyclic copolymers.

Compound (B) is advantageously a diorganopolysiloxane containing at least two lower (for example $C_2$-$C_4$) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane/dimethylsiloxane copolymers, dimethylvinylsiloxy-terminated dimethylpolysiloxanes, dimethylvinylsiloxy-terminated dimethylsiloxane/methylphenylsiloxane copolymers, dimethylvinylsiloxy-terminated dimethylsiloxane/diphenylsiloxane/methylvinylsiloxane copolymers, trimethylsiloxy-terminated dimethylsiloxane/methylvinylsiloxane copolymers, trimethylsiloxy-terminated dimethylsiloxane/methylphenylsiloxane/methylvinylsiloxane copolymers, dimethylvinylsiloxy-terminated methyl(3,3,3-trifluoropropyl)polysiloxanes, and dimethylvinylsiloxy-terminated dimethylsiloxane/methyl(3,3,3-trifluoropropyl)siloxane copolymers.

In particular, the elastomeric organopolysiloxane may be obtained via reaction of dimethylvinylsiloxy-terminated dimethylpolysiloxane and of trimethylsiloxy-terminated methylhydrogenopolysiloxane, in the presence of a platinum catalyst.

Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer may be a non-emulsifying elastomer.

The term "non-emulsifying" defines organopolysiloxane elastomers not containing a hydrophilic chain and in particular not containing polyoxyalkylene units (especially polyoxyethylene or polyoxypropylene units) or a polyglyceryl unit. Thus, according to a specific form of the invention, the composition comprises an organopolysiloxane elastomer devoid of polyoxyalkylene units and of polyglyceryl unit.

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are described in particular in patents EP 242 219, EP 285 886 and EP 765 656 and in application JP-A-61-194009.

The silicone elastomer is generally in the form of a gel, a paste or a powder, in particular in the form of a gel in which the silicone elastomer is dispersed in a linear (dimethicone) or cyclic (e.g.: cyclopentasiloxane) silicone oil. Non-emulsifying elastomers that may more particularly be mentioned include those sold under the names KSG-6, KSG-15, KSG-16, KSG-18, KSG-41, KSG-42, KSG-43 and KSG-44, by the company Shin-Etsu, DC9040 and DC9041 by the company Dow Corning, and SFE 839 by the company General Electric.

A gel of silicone elastomer dispersed in a silicone oil may be chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

The organopolysiloxane elastomer particles may also be used in powder form: mention may be made especially of the powders sold under the names Dow Corning 9505 Powder and Dow Corning 9506 Powder by the company Dow Corning, these powders having the INCI name: dimethicone/vinyl dimethicone crosspolymer.

The organopolysiloxane powder may also be coated with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and have the INCI name: Vinyl Dimethicone/Methicone Silsesquioxane Crosspolymer.

As examples of organopolysiloxane powders coated with silsesquioxane resin according to the invention, mention may be made especially of the organopolysiloxane elastomers having the INCI name Vinyl Dimethicone/Methicone Silsesquioxane Crosspolymer, such as those sold under the commercial reference KSP-100 from the company Shin-Etsu.

As lipophilic gelling agent of organopolysiloxane elastomer type, mention may be made especially of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), Vinyl Dimethicone/Methicone Silsesquioxane Crosspolymer, Diphenylsiloxy Phenyl Trimethicone (and) Dimethicone (and) Phenyl Vinyl Dimethicone Crosspolymer (INCI name) and in particular Dimethicone Crosspolymer (INCI name).

The composition according to the invention comprises from 7% to 25% by weight of at least one polyol relative to the total weight of the composition.

For the purposes of the present invention, the term "polyol" should be understood as meaning any organic molecule, preferably C3-C8, comprising at least two free hydroxyl groups.

A polyol that is suitable for use in the invention may be a compound of linear, branched or cyclic, saturated or unsaturated hydrocarboned chain, bearing on the alkyl chain at least two —OH functions. Preferably, a polyol that may be used in the composition according to the invention is a compound of linear alkyl type bearing on the alkyl chain at least two —OH functions, preferably two —OH functions.

The polyols that are advantageously suitable for formulating the cosmetic compositions according to the present invention are those especially containing from 2 to 16 carbon atoms and preferably 3 to 8 carbon atoms.

The polyols that may be used according to the present invention are chosen from polyols containing from 3 to 8 carbon atoms. Mention may be made especially of:
diols, such as propylene glycol, butylene glycol, pentylene glycol, dipropylene glycol, hexylene glycol and 1,3-propanediol;
triols, such as glycerol (glycerin);
and mixtures thereof.

According to a preferred mode, use will be made of 1,3-propanediol, pentylene glycol, glycerol, and mixtures thereof.

According to a particular mode, the polyol is pentylene glycol.

The composition preferably comprises from 7% to 20% and particularly from 10% to 17% by weight of at least one polyol relative to the total weight of the composition.

In one particular embodiment, the composition according to the invention comprises at least one polyol which is chosen from linear polyols comprising at least two —OH functions and comprising from 3 to 8 carbon atoms, such as propylene glycol, 1,3-propanediol, and mixtures thereof, preferably in a content of from 7% to 15% by weight relative to the total weight of the composition, in particular in a content of from 11% to 15% by weight relative to the total weight of the composition.

The composition according to the invention comprises at least two nonionic surfactants that are different from each other, and in particular comprises at least one nonionic surfactant of ester type and at least one nonionic surfactant chosen from a fatty alcohol.

The composition according to the invention thus comprises at least one nonionic surfactant of ester type, which is especially a mixture of at least one ester obtained by esterification of a solid wax with a polyol, of a fatty acid diester with a polyglycerol, of a jojoba wax (preferably of an ester of jojoba wax) and of a fatty alcohol. Said ester is nonionic.

Said nonionic surfactant of ester type according to the invention comprises: i) at least one unsaturated ester, preferably monounsaturated, of formula (A):

in which:
$R^1$ and $R^2$ represent, respectively, a C18 to C44 fatty chain, and at least $R^1$ or $R^2$ is monounsaturated;
ii) at least one polyglycerol diester of formula (B):

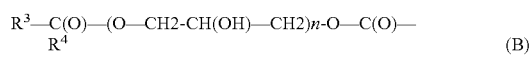

in which:
n=2 to 6
$R^3$ and $R^4$ represent, respectively, a saturated, linear or branched C18 to C44 fatty chain, and
iii) at least one C10-C30 fatty alcohol.

According to the present invention insaturated ester of formula (A) comprises at least one insaturated ester, preferably monounsaturated or di-unsaturated.

Preferably $R^1$ and $R^2$ represent, respectively, one C18 to C44 fatty chain or their mixtures thereof.

According to a particular mode of the invention, in formula (A), $R^1$ and $R^2$ represent, respectively, a C18 to C40 fatty chain, preferably a C18-C30 fatty chain. At least one of the radicals $R^1$ or $R^2$ is monounsaturated.

More specifically, in formula (A), the group $R^1$—C(O) corresponds to the carbon chain of the fatty acid. This chain may be linear or monounsaturated, and comprises at least 18 carbon atoms, preferably comprises 18 to 44 carbon atoms. Mention may be made of oleic acid (C18:1), gadoleic acid (C20:1), erucic acid (C22:1) up to hexacosanoic acid (C26:1) for the unsaturated acids. The group R—C(O) may also be derived from branched and saturated acids of at least 18 carbon atoms, also known as Guerbet acids. The group $R^2$—O— may be derived from linear monounsaturated fatty alcohols containing at least 18 carbon atoms. Mention may thus be made of octadecenol, eicosenol, docosenol and hexacosenol. The carbon chain of the alcohol may also be branched and saturated and contain at least 18 carbon atoms. Such alcohols are also known as Guerbet alcohols.

Preferably, the unsaturated, preferably monounsaturated, ester of formula (A) is a mixture of esters comprising different fatty chain lengths in their structures. More preferably, such a ounsaturated ester is liquid at room temperature.

A preferred unsaturated, preferably monounsaturated, ester that may be mentioned, for example, is the product commonly known as jojoba oil (or jojoba esters), the liquid nature being due to the presence of monounsaturated chains. This oil in particular comprises esters of unsaturated C18:1 (preferably in minor amount), C20:1 and C22:1 (preferably in major amount with C20:1>C22:1) fatty acids with unsaturated C20:1, C22:1 and C24:1 fatty alcohols.

According to one embodiment, in formula (B), the group $R^3$—C(O)— corresponds to the carbon chain of a C18 to C44 fatty acid, said acid usually being linear and saturated, preferably corresponding to a linear and unsaturated C20 to C34 fatty acid. It thus comprises eicosanoic acid (or arachidic acid) (C20), docosanoic acid (or behenic acid) (C22), tetracosanoic acid (or lignoceric acid) (C24), and hexacosanoic acid (or cerotic acid) (C26). The group $R^4$ corresponds to the hydrocarbon-based chain of the alcohol, said alcohol usually being saturated, linear and bearing a C18 to C44 chain, preferably a C20 to C34 chain. N is an integer between 2 and 6.

According to the present invention, the ester derived from the esterification of sloid wax and polyol (in particular polyglycerol) is obtained by esterification of a solid wax in the presence of at least one polyol.

The wax under consideration in the context of the present invention is generally a lipophilic compound that is solid at room temperature (25° C.), with a solid/liquid reversible change of state, having a melting point of greater than or equal to 30° C., preferably greater than or equal to 40° C., which may be up to 200° C. and in particular up to 120° C.

Depending on the source of the wax, the mixture of monoesters may also comprise a certain proportion of esters of hydroxy acids such as hydroxypalmitic acid or hydroxystearic acid.

This is the case, for example, for beeswax. Preferably, said alcohol is eicosanol, docosanol or tetracosanol. Beeswax, carnauba wax, candelilla wax, rice bran wax, sunflower wax, ouricury wax, shellac wax and sugarcane wax are examples of natural solid waxes. Preferably, the solid wax is beeswax.

The solid waxes have a melting point of between 50 and 90° C. They correspond to mixtures mainly comprising monoesters having the formula $R^1$—C(O)—O—$R^2$, in which the group $R^1$—C(O)— corresponds to the carbon chain of the fatty acid, said fatty acid usually being linear and saturated and containing a number of carbon atoms of at least 18, in particular 20, preferably up to 44 and preferably up to 34. They thus include eicosanoic acid (or arachidic acid) (C20), docosanoic acid (or behenic acid) (C22), tetracosanoic acid (or lignoceric acid) (C24), and hexacosanoic acid (or cerotic acid) (C26). Depending on the source of the wax, the mixture of monoesters may also comprise a certain proportion of esters of hydroxy acids such as hydroxypalmitic acid or hydroxystearic acid. This is the case, for example, for beeswax. The group $R^2$ corresponds to the hydrocarbon-based chain of the alcohol, said alcohol usually being saturated, linear and bearing a number of carbon atoms of at least 18, in particular 20, preferably up to 44 and preferably up to 34. Preferably, said alcohol is eicosanol, docosanol or tetracosanol. Beeswax, carnauba wax, candelilla wax, rice bran wax, sunflower wax, ouricury wax, shellac wax and sugarcane wax are examples of natural solid waxes. Preferably, the solid wax is beeswax.

Preferably, the polyol used for the esterification is selected from the group constituted of ethylene glycol, diethylene glycol, triethylene glycol, 2-methylpropanediol, propylene glycol, butylene glycol, neopentyl glycol, hexylene glycol, octylene glycol, polyethylene glycol, polypropylene glycol, trimethylolpropane, sorbitol, erythritol, pentaerythritol, dipentaerythritol, glycerol, diglycerol and polyglycerol (i.e. a polymer with glycerol units, preferably 2-10 units). More preferably, the polyol is a polyglycerol, with a mean degree of polymerization of between 2 and 5, preferably of 3. Preferably, the polyol is polyglycerol-3.

The nonionic ester surfactant also comprises the acid part of a solid wax. Waxes have a complex composition. They have the common characteristic of containing a mixture of monoesters of very long chain fatty acids and fatty alcohols.

Preferably, the nonionic ester surfactant is a wax derivative obtained by reacting together at least one solid wax and at least one unsaturated, preferably monounsaturated, ester of formula (A) in the presence of at least one polyol and optionally at least one catalyst. In such a case, a transesterification reaction takes place between the various chemical species to give the wax derivative.

The preferred catalysts are alkaline or alkali metal hydroxides or alkoxides, calcium hydroxide, potassium carbonate, sodium carbonate or tin-based or titanium-based catalysts.

Preferably, the solid wax is advantageously chosen from the group constituted of carnauba wax, candelilla wax, rice bran wax, sunflower wax, sugarcane wax, ouricury wax, beeswax and shellac wax.

In a preferred embodiment, the wax derivative is obtained by reacting jojoba wax, beeswax and a polyglycerol, such as polyglycerol-3.

In practice, the reaction of transesterification is preferably performed at a temperature of between 100° C. and 220° C., advantageously between 150° C. and 200° C. Preferably, the liquid wax/solid wax mass ratio ranges between 5/95 and 95/5, advantageously between 30/70 and 75/25. The wax/polyol mass ratio preferably ranges between 1/99 and 99/1, advantageously between 95/5 and 50/50. Preferably, the proportion of esterified polyol represents between 0.5% and 50% by weight of the mixture, the proportion of esterified fatty acids represents between 20% and 60% by weight of the mixture and the proportion of esterified fatty alcohols represents between 20% and 60% by weight of the mixture.

Preferably, the nonionic ester surfactant is also present with a diester of a C14-C22 fatty acid with a polyglycerol.

Typically, the C14-C22 fatty acid may be chosen from the group constituted of myristate acid, stearic acid, isostearic acid, palmitic acid, oleic acid, behenic acid, erucic acid and arachidic acid, and mixtures thereof.

The polyglycerol may be a polymer of glycerol units, preferably a polymer with a mean degree of polymerization of between 4 and 8, preferably of 6.

Preferably, said diester is a diester of distearic acid with hexaglycerol. Preferably, it is polyglyceryl-6 distearate.

According to a particular mode of the invention, the composition according to the invention may also be constituted of at least one fatty alcohol containing from 10 to 30 carbon atoms.

As examples of fatty alcohols that may be used, mention may be made of linear or branched fatty alcohols, of synthetic origin or alternatively of natural origin, for example alcohols derived from plant materials (coconut, palm kernel, palm, etc.) or from animal materials (tallow, etc.). Use is preferably made of a fatty alcohol comprising from 20 to 26 carbon atoms, preferably from 10 to 24 carbon atoms and more preferably from 12 to 22 carbon atoms.

As particular examples of fatty alcohols that may be used in the context of the present invention, mention may be made in particular of lauryl alcohol, myristyl alcohol, cetyl alcohol, stearyl alcohol, isostearyl alcohol, palmityl alcohol, oleyl alcohol, cetearyl alcohol (mixture of cetyl alcohol and stearyl alcohol), behenyl alcohol, erucyl alcohol and arachidyl alcohol, and mixtures thereof.

Furthermore, it is most particularly advantageous according to the present invention to use in combination a mixture of polyglyceryl-6 distearate and of polyglyceryl-3 beeswax, with cetyl alcohol and jojoba wax.

Among the mixtures that are particularly preferred, mention may be made of the product sold by the company Gattefossé under the name Emulium Mellifera®, comprising jojoba wax, cetyl alcohol, polyglyceryl-6 distearate and polyglyceryl-3 beeswax (INCI name: Polyglyceryl-6 Distearate (and) Jojoba Esters (and) Polyglyceryl-3 Beeswax (and) Cetyl Alcohol).

Said mixture especially comprises from 5% to 30% by weight, relative to the total weight of said mixture, of jojoba wax, from 3% to 15% by weight of cetyl alcohol, at least 50% by weight of polyglyceryl-6 distearate and from 3% to 15% by weight of polyglyceryl-3 beeswax.

The nonionic surfactant of ester type may be present in a composition of the invention in an amount ranging from 1% to 6% by weight, preferably from 2.5% to 3.5% by weight, and in particular 3% by weight, relative to the total weight of the composition.

The composition according to the invention comprises at least one other nonionic surfactant chosen from fatty alcohols; preferably, the composition according to the invention comprises behenyl alcohol.

For the purposes of the invention, the fatty alcohols are solid at room temperature, and saturated and linear, and comprise from 14 to 26 carbon atoms and more particularly from 16 to 22 carbon atoms.

The fatty alcohol(s) that are suitable for use in the invention are preferably chosen from the group comprising cetyl alcohol, stearyl alcohol, cetylstearyl alcohol, myristyl alcohol, tridecyl alcohol, pentadecyl alcohol, heptadecyl alcohol, arachidyl alcohol, behenyl alcohol and myricyl alcohol.

Preferably, the fatty alcohol(s) are chosen from cetyl alcohol, behenyl alcohol, stearyl alcohol and cetylstearyl alcohol, and a mixture thereof.

Particularly preferably, the composition according to the invention comprises a fatty alcohol, which is behenyl alcohol.

In a particular embodiment, the composition according to the invention comprises at least two fatty alcohols that are different from each other, behenyl alcohol and at least one fatty alcohol that is solid at room temperature, saturated and linear, with a carbon chain of 16 to 22 carbon atoms, in particular behenyl alcohol, and a fatty alcohol chosen from cetyl alcohol, stearyl alcohol, cetylstearyl alcohol, and a mixture thereof, preferably behenyl alcohol and cetyl alcohol.

As cetyl alcohols that are most particularly suitable for use in the invention, use may be made, for example, of those sold under the names Ecorol® 16/98 F and Ecorol® 16/98 P sold by the company Ecogreen Oleochemicals, Tegoalkanol® 16 sold by the company Evonik Goldschmidt, Lanette® 16 sold by the company BASF, Vegarol® 1698 sold by the company WF, Alkonat® 1698 P sold by the company Oxiteno, Cetyl Alcohol 98% Min sold by the company Emery Oleochemicals, Ginol® 16 (98%) sold by the company Godrej Industries, Nacol® 16-98 sold by the company Sasol, Kalcol® 6098 sold by the company Kao, and Acilol® 16 sold by the company Aegis Chemical.

As stearyl alcohols that are most particularly suitable for use in the invention, use may be made, for example, of those sold under the names Tegoalkanol® 18 sold by the company Evonik Goldschmidt, Ecorol® 18/98 F and Ecorol® 18/98 P sold by the company Ecogreen Oleochemicals, Lanette® 18 sold by the company BASF, Kalcol® 8098 sold by the company Kao, Acilol® 18 sold by the company Aegis Chemical, Nacol® 18-98 sold by the company Sasol and NAA® 45 sold by the company Nihon Yushi.

As cetylstearyl alcohols that are most particularly suitable for use in the invention, use may be made, for example, of those sold under the names Ecorol® 68/50 F and Ecorol® 68/50 P sold by the company Ecogreen Oleochemicals, Lanette® O OR and Lanette® O OR Flakes sold by the company Cognis, Alkonat® 1618 C50 P sold by the company Oxiteno, Nafol® 16-18 EN sold by the company Sasol, Alcohol Cetoestearilico 50/50 sold by the company Industria Quimica Del Centro, Conol® 30 CK sold by the company New Japan Chemical, Cetylstearyl Alcohol 50:50 sold by the company Evonik Goldschmidt, Kalcol® 6850 sold by the company Kao, Vegarol® 1618 (50:50) sold by the company WF and Ginol® 1618 50:50 OR sold by the company Godrej Industries.

As behenyl alcohol that is most particularly suitable for use in the invention, use may be made, for example, of the product sold under the name Lanette® 22 sold by the company BASF.

The composition according to the invention comprises a content of behenyl alcohol ranging from 0.5% to 10% by weight, in particular from 1% to 7% by weight, and preferably ranging from 1% to 3% by weight, relative to the total weight of the composition.

The composition according to the invention comprises a content of total fatty alcohol(s) ranging from 0.5% to 15% by weight, in particular ranging from 1% to 10% by weight and preferably ranging from 2% to 5% by weight relative to the total weight of the composition.

The emulsifying system of the invention may also comprise at least one co-surfactant chosen from anionic surfactants in addition and preferably different of surfactants according to the invention, especially chosen from surfactants of the types such as glutamic acid salts, salts of esters of phosphoric acid and of fatty alcohol, and alkyl sulfates, and mixtures thereof.

1. Anionic Surfactant of Glutamic Acid Salt Type

According to one embodiment, a composition in accordance with the invention may comprise at least one glutamic acid salt or, in particular, an acylglutamic salt (INCI name: acyl glutamic acid).

The ones that are especially suitable for use in the invention are acylglutamic acids in which the acyl group comprises from 10 to 30 carbon atoms, preferably from 12 to 22 carbon atoms, for instance lauroylglutamic acid, myristoylglutamic acid, palmitoylglutamic acid, stearoylglutamic acid, behenoylglutamic acid, olivoylglutamic acid, cocoylglutamic acid, and the salts of these acids, especially the salts of alkali metals such as Na, Li or K, preferably Na or K, the salts of alkaline-earth metals such as Mg, or the ammonium salts of said acids.

Advantageously, a composition according to the invention comprises as anionic surfactant at least one glutamate, said glutamate containing a C8 to C20 alkyl chain, and a solubilizing counter-cation chosen from sodium, potassium and ammonium.

Such anionic surfactants are those described in EP 2 335 681.

As illustrations of these glutamate salts, mention may be made most particularly of the anionic surfactants chosen from potassium cocoyl glutamates, potassium methyl cocoyl glutamate, sodium methyl caproyl glutamate, sodium cocoyl glutamate, sodium lauroyl glutamate, sodium methyl cocoyl glutamate, sodium methyl lauroyl glutomate, sodium methyl myristoyl glutamate, sodium methyl oleyl glutamate, sodium palmitoyl methyl glutamate, sodium methyl stearoyl glutamate, and mixtures thereof.

More particularly, the anionic surfactants are chosen from potassium cocoyl glutamates, potassium methyl cocoyl glutamate, sodium cocoyl glutamate, sodium lauroyl glutamate, sodium methyl cocoyl glutamate, sodium lauroyl methyl glutamate, and mixtures thereof.

According to one embodiment of the invention, at least one anionic surfactant is chosen from sodium methyl oleoyl glutamates, sodium N-myristoyl-N-methyl glutamate, the sodium salt of the fatty acid methyl glutamate of coconut oil and sodium lauryl methyl glutamate.

Such compounds are sold under the name Amisoft by the company Ajinomoto and in particular under the references Amisoft CA, Amisoft LA, Amisoft HS 11 PF, Amisoft MK-11, Amisoft LK-11 and Amisoft CK-11, or alternatively under the name Eumulgin SG by the company Cognis.

Mention may also be made of triethanolamine cocoyl glutamate sold under the name Amisoft CT12 by the company Ajinomoto, and triethanolamine lauroyl glutamate sold especially under the name Acylglutamate LT-12 by the company Ajinomoto.

As acylglutamic acid salt, mention may also be made of the product sold under the reference Acylglutamate HS 11 by the company Ajinomoto and the product sold under the reference Acylglutamate HS-21 by the company Ajinomoto.

Mention may also be made of the mixture of acylglutamate salts, such as Amisoft LS-22 sold by Ajinomoto.

Needless to say, the compositions of the present invention may also comprise mixtures of anionic surfactants of glutamate type, such as the mixture of anionic surfactants of glutamate and taurate type, a mixture of glutamates, or a mixture of surfactants of glutamate and sarcosinate type.

According to a preferred embodiment, a composition according to the invention comprises the monosodium salt of N-stearoyl-L-glutamic acid, more particularly the product sold by the company Ajinomoto under the reference Amisoft HS 11 PF.

The acylglutamic acid(s) and salts thereof may be present in the composition in accordance with the invention in an active material (AM) content ranging from 0.01% to 5% by weight and preferably from 0.1% to 1% by weight relative to the total weight of the composition.

2. Anionic Surfactant of the Type Such as Salts of Esters of Phosphoric Acid and of Fatty Alcohol These surfactants are advantageously alkaline salts of esters of phosphoric acid and of a fatty alcohol comprising from 14 to 36 carbon atoms, preferably from 16 to 18 carbon atoms, such as cetyl alcohol or myristyl alcohol.

In particular, they may be chosen from:

the sodium and potassium salts of monocetyl phosphate, for instance the compound sold under the reference Amphisol K by the company DSM;

alkaline salts of dicetyl phosphate, and in particular the sodium and potassium salts;

alkaline salts of dimyristyl phosphate, and in particular the sodium and potassium salts;

alkaline salts of cholesteryl sulfate, and in particular the sodium salt; alkaline salts of cholesteryl phosphate, and in particular the sodium salt; and the alkylsulfonic derivatives of formula (I):

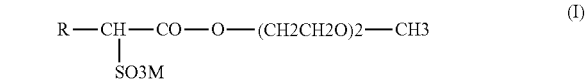

in which R represents C16H33 and C18H37 radicals taken together or separately, and M is an alkali metal, preferably sodium.

Preferably, this type of surfactant is chosen from alkaline salts of esters of phosphoric acid and of a fatty alcohol comprising from 14 to 36 carbon atoms, preferably from 16 to 18 carbon atoms, such as cetyl alcohol or myristyl alcohol, and in particular the sodium and potassium salts of monocetyl phosphate.

3. Surfactants of Alkyl Sulfate Type

This type of surfactant is most particularly chosen from alkyl ether sulfates. Examples that may be mentioned include sodium lauryl ether sulfate (70/30 C12-14) (2.2 OE), for instance the product sold under the name Sipon AOS225 or Texapon N702 by the company Henkel, ammonium lauryl ether sulfate (70/30 C12-14) (3 OE), for instance the product sold under the name Sipon LEA 370 by the company Henkel, ammonium (C12-C14)alkyl ether (9 OE) sulfate, for instance the product sold under the name Rhodapex AB/20 by the company Rhodia Chimie, and the mixture of sodium magnesium lauryl and oleyl ether sulfate, for instance the product sold under the name Empicol BSD 52 by the company Albright & Wilson.

According to one embodiment variant, a composition according to the invention comprises at least one anionic surfactant chosen from triethanolamine cocoyl glutamate, triethanolamine lauroyl glutamate, monocetyl phosphate, the combination of the monosodium salt of N-stearoyl-L-glutamic acid, and mixtures thereof.

The composition according to the invention comprises one or more gelling agents.

The total solids content of gelling agent(s) in the composition according to the invention may range from 0.05% to 15% by weight, preferably from 0.1% to 10% by weight, more preferentially from 0.2% to 7% by weight and better still from 0.5% to 5% by weight relative to the total weight of the composition.

According to one embodiment, the total solids content of gelling agent(s) in the composition according to the invention is greater than or equal to 0.5% by weight, preferably greater than or equal to 0.8% by weight, and better still greater than or equal to 1% by weight, relative to the total weight of the composition.

The gelling agent (or thickener) may be chosen especially from:

1) Polyacrylate Salts

These are in particular crosslinked and neutralized polymers, in non-particulate form.

The sodium salts are advantageously preferred.

Examples that may be mentioned include the polymers bearing the INCI name Sodium polyacrylate, for instance:
  Cosmedia SP® or crosslinked sodium polyacrylate containing 90% solids and 10% water, Cosmedia SPL® or sodium polyacrylate as an inverse emulsion containing about 60% dry active material, an oil (hydrogenated polydecene) and a surfactant (PPG-5 laureth-5), both sold by the company Cognis,
  partially neutralized crosslinked sodium polyacrylates that are in the form of an inverse emulsion comprising at least one polar oil, for example the product sold under the name Luvigel® EM sold by the company BASF.

The polyacrylate salts may be present in the composition according to the invention in a solids amount ranging from 0.1% to 3% by weight and more particularly from 0.1% to 2% by weight relative to the total weight of the composition.

2) Optionally Crosslinked and/or Neutralized 2-Acrylamido-2-Methylpropanesulfonic Acid (AMPS) Polymers and Copolymers, Chosen from:

a) poly(2-acrylamido-2-methylpropanesulfonic acid) polymers, in particular crosslinked and at least 90% neutralized polyAMPS homopolymers.

They are generally characterized in that they comprise, randomly distributed:
  i) from 90% to 99.9% by weight of units of general formula (1) below:

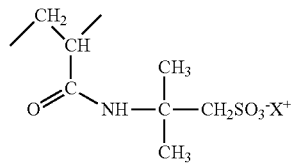

in which X+ denotes a cation or a mixture of cations, not more than 10 mol % of the cations X+ possibly being protons H+; and
  ii) from 0.01% to 10% by weight of crosslinking units originating from at least one monomer containing at least two olefinic double bonds; the weight proportions being defined relative to the total weight of the polymer.

This polymer preferably comprises from 98% to 99.5% by weight of units of formula (1) and from 0.2% to 2% by weight of crosslinking units.

The cation X+ represents a cation or a mixture of cations chosen in particular from a proton, an alkali metal cation, a cation equivalent to that of an alkaline-earth metal, or the ammonium ion. The preferential cation X+ is the NH4+ cation. More particularly, 90 mol % to 100 mol % of the cations are NH4+ cations and from 0 to 10 mol % are protons (H+).

The crosslinking monomers bearing at least two olefinic double bonds are chosen, for example, from dipropylene glycol diallyl ether, polyglycol diallyl ethers, triethylene glycol divinyl ether, hydroquinone diallyl ether, tetraallyloxyethane or other polyfunctional alcohol allyl or vinyl ethers, tetraethylene glycol diacrylate, triallylamine, trimethylolpropane diallyl ether, methylenebisacrylamide or divinylbenzene.

The crosslinking monomers bearing at least two olefinic double bonds are more particularly chosen from those corresponding to the general formula (2) below:

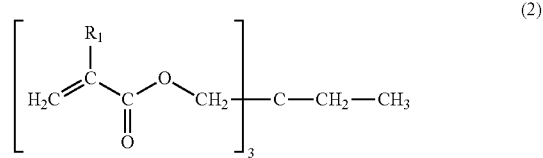

in which R1 denotes a hydrogen atom or a C1-C4 alkyl radical and more particularly a methyl (trimethylolpropane triacrylate) radical.

A polymer of this type that may in particular be mentioned is the crosslinked and neutralized 2-acrylamido-2-methylpropanesulfonic acid homopolymer sold by the company Clariant under the trade name Hostacerin® AMPS (CTFA name: ammonium polyacryldimethyltauramide).

b) copolymers of acrylamide and of AMPS, in particular crosslinked anionic copolymers of acrylamide and of AMPS.

These copolymers may especially be crosslinked with a polyolefinically unsaturated compound such as those chosen from the group constituted by tetraallyloxyethane, allylpentaerythritol, methylenebisacrylamide, allyl sucrose and pentaerythritol. Use is preferentially made of methylenebisacrylamide, partially or totally neutralized with a neutralizing agent such as sodium hydroxide, potassium hydroxide, aqueous ammonia or an amine such as triethanolamine.

Preferably, said polyolefinically unsaturated compound is present in the copolymer in a concentration of between 0.06 and 1 mmol per mole of the monomer mixture.

The preferred copolymers are obtained by radical copolymerization of 15-85 mol % of acrylamide and of 15-85 mol % of 2-acrylamido-2-methylpropanesulfonic acid, especially 30-70 mol % of acrylamide and 30-70 mol % of 2-acrylamido-2-methylpropanesulfonic acid, and better still 55-70 mol % of acrylamide and 30-45 mol % of 2-acrylamido-2-methylpropanesulfonic acid.

Moreover, the 2-acrylamido-2-methylpropanesulfonic acid may be generally at least partially neutralized in the form of a salt, for example with sodium hydroxide, with potassium hydroxide or with a low molecular weight amine such as triethanolamine, or mixtures thereof.

The gelling agent that may be used may also be chosen from crosslinked anionic copolymers of acrylamide and of 2-acrylamido-2-methylpropanesulfonic acid.

A crosslinked copolymer that is particularly preferred in the context of the implementation of the present invention is especially available under the name Sepigel 305 sold by SEPPIC (CTFA name: polyacrylamide/C13-14 isoparaffin/ Laureth 7); mention may also be made of the product Simulgel 600 (CTFA name: Acrylamide/Sodium acryloyldimethyltaurate copolymer/Isohexadecane/Polysorbate 80) sold by SEPPIC;

c) copolymers derived from crosslinked or non-crosslinked 2-acrylamido-2-methylpropanesulfonic acid (AMPS), comprising at least one hydrophobic group comprising i) from 80 mol % to 99 mol % of 2-acrylamido-2-methylpropanesulfonic acid (AMPS) units of formula (3) below:

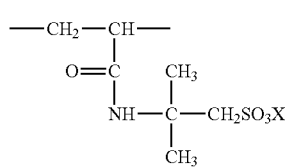

(3)

in which X+ is a proton, an alkali metal cation, an alkaline-earth metal cation or the ammonium ion; it being understood that when X represents an alkaline-earth metal cation, it shares two positive charges with two $SO_3$ groups; and ii) from 1 mol % to 20 mol % and preferably from 1 mol % to 15 mol % of units of formula (3bis) below:

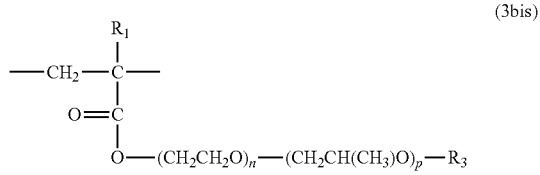

(3bis)

in which n and p, independently of each other, denote a number of moles and range from 0 to 30 and preferably from 1 to 20, with the proviso that n+p is less than or equal to 30, preferably less than 25 and better still less than 20; R1 denotes a hydrogen atom or a linear or branched C1-C6 alkyl radical (preferably methyl) and R3 denotes a linear or branched alkyl group comprising m carbon atoms, with m ranging from 6 to 30 and preferably from 10 to 25 carbon atoms.

These polymers are preferentially partially or totally neutralized with a mineral base, for instance sodium hydroxide, potassium hydroxide or aqueous ammonia, or with an organic base such as monoethanolamine, diethanolamine, triethanolamine, aminomethylpropanediol, N-methylglucamine, or basic amino acids, for instance arginine and lysine, and mixtures thereof.

When the polymer is crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

As AMPS-based polymers that may be used in the composition according to the invention, mention may be made of the polymers prepared from 2-acrylamido-2-methylpropanesulfonic acid (AMPS) or a sodium or ammonium salt thereof, with an ester of (meth)acrylic acid and of an oxyethylenated C10 to C20 alcohol comprising from 6 to 25 oxyethylene groups.

Mention may be made in particular of the polymers prepared from 2-acrylamido-2-methylpropanesulfonic acid (AMPS), or a sodium or ammonium salt thereof, with an ester of (meth)acrylic acid and:

of a C10-C18 alcohol oxyethylenated with 8 mol of ethylene oxide (Genapol C-080 from the company Clariant), of a C11 oxo alcohol oxyethylenated with 8 mol of ethylene oxide (Genapol UD-080 from the company Clariant), of a C11 oxo alcohol oxyethylenated with 7 mol of ethylene oxide (Genapol UD-070 from the company Clariant), of a C12-C14 alcohol oxyethylenated with 7 mol of ethylene oxide (Genapol LA-070 from the company Clariant), of a C12-C14 alcohol oxyethylenated with 9 mol of ethylene oxide (Genapol LA-090 from the company Clariant), of a C12-C14 alcohol oxyethylenated with 11 mol of ethylene oxide (Genapol LA-110 from the company Clariant), of a C16-C18 alcohol oxyethylenated with 8 mol of ethylene oxide (Genapol T-080 from the company Clariant), of a C16-C18 alcohol oxyethylenated with 11 mol of ethylene oxide (Genapol T-110 from the company Clariant), of a C16-C18 alcohol oxyethylenated with 15 mol of ethylene oxide (Genapol T-150 from the company Clariant), of a C16-C18 alcohol oxyethylenated with 20 mol of ethylene oxide (Genapol T-200 from the company Clariant), of a C16-C18 alcohol oxyethylenated with 25 mol of ethylene oxide (Genapol T-250 from the company Clariant), of a C18-C22 alcohol oxyethylenated with 25 mol of ethylene oxide, of a C16-C18 isoalcohol oxyethylenated with 25 mol of ethylene oxide.

According to one embodiment, the AMPS-based polymer is a copolymer of AMPS and of a C16-C18 alkyl methacrylate comprising from 6 to 25 oxyethylene groups, obtained from methacrylic acid or a methacrylic acid salt and from a C16-C18 alcohol oxyethylenated with 6 to 25 mol of ethylene oxide. The amphiphilic polymer may also be a copolymer of AMPS and of a C12-C14 alkyl methacrylate comprising from 6 to 25 oxyethylene groups, obtained from methacrylic acid or a methacrylic acid salt and from a C12-C14 alcohol oxyethylenated with 6 to 25 mol of ethylene oxide.

Mention may in particular be made of:
the non-crosslinked copolymer obtained from 92.65 mol % of AMPS and 7.35 mol % of a C16-C18 alkyl methacrylate comprising 8 oxyethylene groups (Genapol T-080), such as the product sold by the company Clariant under the name Aristoflex SNC;
the non-crosslinked copolymer obtained from 91.5 mol % of AMPS and 8.5 mol % of a C12-C14 alkyl methacrylate comprising 7 oxyethylene groups (Genapol LA-070), such as the product sold by the company Clariant under the name Aristoflex LNC;
and mixtures thereof.

As crosslinked AMPS polymers of this type, mention may be made more especially of the product sold under the name Aristoflex HMS by the company Clariant, which is a crosslinked AMPS/ethoxylated (25 EO) stearyl methacrylate copolymer, or the product sold under the name Aristoflex HMB by the company Clariant, which is a crosslinked AMPS/ethoxylated (25 OE) behenyl methacrylate copolymer. A mixture of these polymers may also be used.

The AMPS polymers and copolymers may be present in the composition according to the invention in a solids amount ranging from 0.1% to 5% by weight and more particularly from 0.1% to 4% by weight relative to the total weight of the composition.

3) Heterogeneous Polyosides

According to the present invention, the term "heterogeneous polyholoside" means polymers constituted of a combination of different saccharides or saccharides having the same chemical empirical formula but different geometrical configurations (for example D and L isomers).

These polymers differ both from polyheterosides, which are constituted of one or more saccharides and of a non-carbohydrate part, and from homogeneous polyholosides, which result from the combination of the same saccharide.

Thus, the heterogeneous polyholoside according to the invention is constituted solely of saccharides and results from the combination of at least two different saccharides.

The polyholosides according to the invention may be constituted of 2 to 10 saccharides, which are compounds commonly known as oligoholosides, or of more than 10 saccharides, which are compounds commonly known as polyholosides.

The saccharides present in the polyholoside according to the invention may be chosen from all the envisageable saccharides, of natural or synthetic origin, and especially such as:
aldoses such as
pentoses: ribose, arabinose, xylose or apiose, for example,
hexoses: glucose, fucose, mannose or galactose, for example,
ketoses such as fructose,
deoxyoses, such as rhamnose, digitoxose, le cymarose or oleandrose,
saccharide derivatives such as uronic acids, for instance mannuronic acid, guluronic acid, galacturonic acid or glycuronic acid, or itols, for instance mannitol or sorbitol.

The polyholoside according to the invention may be branched or linear. It may also be substituted, for example with fatty chains, especially comprising 8 to 30 carbon atoms.

Moreover, the polyholoside according to the invention may be an alginate (poly mannuronate and guluronate) such as a sodium alginate, a propylene glycol alginate, a calcium alginate or a glyceryl alginate.

However, the heterogeneous polyholoside preferably comprises at least one fucose unit, which may be present in an amount of 10-90% by weight, preferably 15-35% by weight, relative to the solids weight of polyholoside.

In particular, the polyholoside according to the invention may comprise fucose, galactose and galacturonic acid units, and, for example, may comprise a linear sequence of α-L-Fucose, of α-D-Galactose and of galacturonic acid. In this case, it preferably has a viscosity of 800-1200 mPa·s (Brookfield LV31 viscosity, 12 rpm, at 30° C.) when it is dissolved in water at a concentration of about 1% by weight. Such a polyholoside is especially available in the form of a solution at 1% in water from the company Solabia under the trade name Fucogel 1000 PP®.

The polyholosides according to the invention are preferably introduced into the composition in the form of an aqueous solution which may comprise from 0.1% to 5% by weight of polyholoside.

The polyholosides may be present in the composition according to the invention in a solids amount ranging more particularly from 0.1% to 10% by weight relative to the total weight of the composition.

4) Glyceryl Acrylate Polymers

These glyceryl acrylate polymers are chosen especially from copolymers of glyceryl acrylate and of acrylic acid. Such copolymers are sold especially under the names Lubrajel® MS, Lubrajel® CG, Lubrajel® DV, Lubrajel® NP, Lubrajel® L Oil, Lubrajel® Oil BG, Lubrajel® PF, Lubrajel® TW and Lubrajel® WA by the company Guardian Laboratories. Use is preferably made of Lubrajel® MS.

The glyceryl acrylate polymers may be present in the composition according to the invention in a solids amount ranging more particularly from 0.1% to 10% by weight relative to the total weight of the composition.

5) Polysaccharides Such as:
algal extracts, such as alginates, carrageenans and agar-agar, and mixtures thereof. Examples of carrageenans that may be mentioned include Satiagum UTC30® and UTC10® from the company Degussa; an alginate that may be mentioned is the sodium alginate sold under the name Kelcosol® by the company ISP;
gums, such as xanthan gum, guar gum and nonionic derivatives thereof (hydroxypropyl guar), gum arabic, konjac gum or mannan gum, gum tragacanth, ghatti gum, karaya gum, locust bean gum; examples that may be mentioned include the guar gum sold under the name Jaguar HP 105® by the company Rhodia; mannan gum and konjac Gum® (1% glucomannan) sold by the company GfN;
modified or unmodified starches, such as those derived, for example, from cereals such as wheat, corn or rice, from legumes such as white lentil, from tubers such as potato or cassava, tapioca starches; dextrins, such as corn dextrins; an example that may especially be mentioned is the rice starch Remy DR I® sold by the company Remy; Amidon de Maïs B® from the company Roquette; potato feculent modified with 2-chloroethylaminodipropionic acid neutralized with sodium hydroxide, sold under the name Structure Solanace® by the company National Starch; native tapioca starch powder sold under the name Tapioca Pure® by the company National Starch;

dextrins, such as dextrin extracted from corn under the name Index® from the company National Starch;

celluloses and derivatives thereof, in particular alkyl- or hydroxyalkyl celluloses; mention may be made especially of methylcelluloses, hydroxyalkylcelluloses, ethylhydroxyethylcelluloses and carboxymethylcelluloses. Examples that may be mentioned include the cetylhydroxyethylcelluloses sold under the names Polysurf 67CS® and Natrosol Plus 330® from Aqualon;

and mixtures thereof.

The polysaccharides may be present in the composition according to the invention in a solids amount ranging from 0.01% to 0.5% by weight and better still from 0.01% to 0.2% by weight relative to the total weight of the composition.

Use is preferably made of gums such as xanthan gum.
6) Modified clays such as modified magnesium silicate (Bentone Gel VS38® from Rheox), or hectorite modified with disteraryldimethylammonium chloride (INCI name: Disteardimonium hectorite) sold under the name Bentone 38 CE by the company Rheox.

The clays may be present in an active material content ranging from 0.05% to 10% by weight and preferentially from 0.1% to 5% by weight relative to the total weight of the composition.

The composition according to the invention may comprise a mixture of the various gelling agents mentioned above.

According to one embodiment, the composition according to the invention comprises at least one gelling agent chosen from:

polymers derived from AMPS copolymers, especially copolymers of acrylamide and of AMPS, in particular crosslinked anionic copolymers of acrylamide and of AMPS, as described above, copolymers based on acrylates derived from the polymerization of at least one C3-C6 monoolefinically unsaturated carboxylic acid monomer or the anhydride thereof and of at least one fatty-chain acrylic acid ester monomer, as described above, and optionally crosslinked, and especially acrylate/C10-C30-alkylacrylate copolymers, and mixtures thereof.

Preferably, the gelling agent is chosen from crosslinked anionic copolymers of acrylamide and of 2-acrylamido-2-methylpropanesulfonic acid.

A crosslinked copolymer that is particularly preferred in the context of the implementation of the present invention is an acid acrylamide/sodium acrylamido-2-methylpropanesulfonate copolymer as an inverse emulsion at 40% in polysorbate 80/I-C13, available especially under the name Simulgel 600® (INCI name: Acrylamide/Sodium acryloyldimethyltaurate copolymer/Isohexadecane/Polysorbate 80) sold by the company SEPPIC.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to keratin materials, such as the skin, the nails, mucous membranes and keratin fibres (such as the eyelashes), especially the skin and the lips.

The physiologically acceptable medium is generally adapted to the nature of the support onto which the composition has to be applied, and also to the appearance under which the composition has to be packaged.

Fatty Phase

A cosmetic composition in accordance with the present invention comprises at least one fatty phase.

The fatty phase of the composition according to the invention comprises at least one wax.

In a particular mode, the fatty phase of the composition according to the invention also comprises at least one synthetic ester such as oils of formula $R_6COOR_5$.

The wax(es) under consideration in the context of the present invention are generally water-insoluble lipophilic compounds that are solid at room temperature (20° C.) and at atmospheric pressure (760 mmHg), with a solid/liquid reversible change of state, having a melting point of greater than or equal to 30° C., which may be up to 200° C. and in particular up to 120° C.

In particular, the waxes that are suitable for use in the invention may have a melting point of greater than or equal to 45° C. and in particular greater than or equal to 55° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name DSC Q2000 by the company TA Instruments.

Preferably, the waxes comprise at least one crystallizable part, which is visible by X-ray diffraction observation.

Preferably, the waxes have an enthalpy of fusion ΔHf of greater than or equal to 70 J/g.

The measurement protocol is as follows:

A sample of 5 mg of wax placed in a crucible is subjected to a first temperature rise passing from −20° C. to 120° C., at a heating rate of 10° C./minute, it is then cooled from 120° C. to −20° C. at a cooling rate of 10° C./minute and is finally subjected to a second temperature rise passing from −20° C. to 120° C. at a heating rate of 5° C./minute. During the second temperature rise, the following parameters are measured:

the melting point (Tf) of the wax as described previously, corresponding to the temperature of the most endothermic peak observed in the melting curve, representing the variation of the difference in power absorbed as a function of the temperature, ΔHf: the heat of fusion of the wax, corresponding to the integral of the entire melting curve obtained. This heat of fusion of the wax is the amount of energy required to make the compound change from the solid state to the liquid state. It is expressed in J/g.

The wax(es) may be hydrocarbon-based waxes, fluoro waxes and/or silicone waxes and may be of plant, mineral, animal and/or synthetic origin.

They may be hydrocarbon-based.

Examples that may especially be mentioned include hydrocarbon-based waxes, for instance beeswax, such as natural beeswax (or bleached beeswax), for instance the product sold under the name White Beeswax SP 453P® by the company Strahl & Pitsch or the product sold under the name Cire d'Abeille Blanche (GR B 889)® by the company Koster Keunen, and synthetic beeswax such as oxyethylenated beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 and 3080 sold by the company Nippon Seiro, ceresins or ozokerites, for instance isoparaffins of which the melting point is below 40° C., such as the product EMW-0003 sold by the company Nippon Seiro, α-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes, the sunflower seed wax sold by the company Koster Keunen under the reference sunflower wax.

Preferably, the composition according to the invention comprises at least one amphiphilic wax.

The term "amphiphilic wax" means a wax comprising at least one hydrophilic part.

The amphiphilic wax(es) may especially be hydrocarbon-based.

The term "hydrocarbon-based wax" means a wax formed essentially from, or even constituted by, carbon and hydrogen atoms, and optionally oxygen and nitrogen atoms, and that does not contain any silicon or fluorine atoms. It may contain alcohol, ester, ether, carboxylic acid, amine and/or amide groups. As hydrocarbon-based wax, a wax chosen from ester waxes and alcohol waxes is in particular preferred.

According to the invention, the term "ester wax" means a wax comprising at least one ester function. According to the invention, the term "alcohol wax" means a wax comprising at least one alcohol function, i.e. comprising at least one free hydroxyl (OH) group.

The amphiphilic wax(es) preferentially used are chosen from hydrocarbon-based waxes esterified with at least one oxyethylenated glycerol group, and mixtures thereof, preferably with at least five oxyethylenated glycerol groups, and mixtures thereof.

The amphiphilic wax(es) preferentially used are chosen from beeswax esterified with at least one oxyethylene and preferably polyoxyethylene group, polyglycerolated beeswax, a polyglycerolated plant wax such as mimosa wax, jojoba wax or sunflower wax, and mixtures thereof.

As wax that may be used according to the invention, mention may be made especially of the mixture of polyglycerolated (3 mol) plant waxes (mimosa/jojoba/sunflower) sold under the name Acticire® by the company Gattefosse (INCI name: Jojoba esters (and) *Helianthus annuus* (sunflower) seed wax (and) polyglycerin-3 (and) *Acacia decurrens* flower wax).

Preferably, the wax(es) are chosen from the group constituted of polyglycerolated plant wax from mimosa, jojoba, sunflower, and mixtures thereof.

Preferably, the composition according to the invention comprises a mixture of polyglycerolated mimosa, sunflower and jojoba waxes, and preferably comprises a mixture of waxes constituted of 50-70% by weight of jojoba wax, 30-40% by weight of sunflower wax and 1-5% by weight of mimosa wax, and 1-5% by weight of polyglycerin-3 relative to the total weight of said mixture.

The wax(es) are present in a total content ranging from 0.5% to 5% by weight, preferably from 1% to 4% by weight, in particular from 2% to 3% by weight and particularly 2.50% by weight, relative to the total weight of the composition.

In the composition according to the invention, the mass ratio [total amount of said nonionic surfactant(s) of ester type]/[total amount of said wax] ranges from 0.8 to 2, preferably from 1 to 1.5.

The synthetic esters according to the present invention are oils of formula $R_6COOR_5$, in which $R_6$ represents a linear or branched fatty acid residue containing from 1 to 40 carbon atoms, and $R_5$ represents a hydrocarbon-based chain that is especially branched, containing from 1 to 40 carbon atoms provided that $R_6+R_5 \geq 10$.

The oils of formula $R_6COOR_5$ may be chosen especially from esters of fatty alcohol and of fatty acid, for instance cetostearyl octanoate, isopropyl alcohol esters, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate.

The oils of formula $R_6COOR_5$ may especially be fatty esters chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

Preferably, the oil(s) of formula $R_6COOR_5$ are chosen from the group constituted of myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

As isononyl isononanoate that is most particularly suitable for use in the invention, use may be made, for example, of the product sold under the name Isononyl Isononanoate (DUB ININ)® from the company Stéarineries Dubois.

As isostearyl neopentanoate that is most particularly suitable for use in the invention, use may be made, for example, of the product sold under the name Isostearyl Neopentanoate (DUB VCI 18®) from the company Stéarineries Dubois.

As isocetyl stearate that is most particularly suitable for use in the invention, use may be made, for example, of the product sold under the name Isocetyl Stearate (DUB SIS16)® from the company Stéarineries Dubois.

As isopropyl palmitate that is most particularly suitable for use in the invention, use may be made, for example, of the product sold under the name Isopropyl Palmitate (DUB IPP)® from the company Stéarineries Dubois.

Preferably, as oil(s) of formula R4COOR5 that are particularly suitable for use in the invention, use may be made of the myristyl/cetyl/stearyl myristate/palmitate/stearate mixture available under the name Crodamol MS-PA® from the company Croda.

The oil(s) of formula $R_6COOR_5$ may be present in a total content ranging from 0.5% to 25% by weight, preferably from 1% to 15% by weight, in particular from 2% to 10% by weight, relative to the total weight of the composition.

The fatty phase generally represents from 5% to 40% by weight, relative to the total weight of the composition, preferably from 10% to 20% by weight, relative to the total weight of said composition.

Aqueous Phase

The composition according to the invention comprises at least 60% by weight, in particular from 60% to 90% by weight and especially from 60% to 80% by weight of water, relative to the total weight of the composition.

The composition according to the invention comprises at least one aqueous phase. The aqueous phase of the composition according to the invention comprises at least water.

For the purposes of the invention, the term "aqueous phase" means water and all the ingredients of the composition of the invention that are soluble in water.

An aqueous phase that is suitable for use in the invention may comprise, for example, a demineralized water, a water chosen from a natural spring water (mineral water and/or thermal water), such as water from La Roche-Posay, water from Vittel or waters from Vichy, and/or a floral water.

The aqueous phase may also comprise at least one additional organic solvent that is miscible with water at room temperature (25° C.), for instance polyols especially containing from 2 to 20 carbon atoms, preferably containing from 2 to 6 carbon atoms, such as glycerol, propylene glycol, isoprene glycol, butylene glycol, pentylene glycol, hexylene glycol, dipropylene glycol, diethylene glycol, caprylyl glycol, sorbitol, polyethylene glycols, polypropylene glycols, and mixtures thereof; glycol ethers (especially containing from 3 to 16 carbon atoms), such as mono-, di- or tripropylene glycol (C1-C4)alkyl ethers, mono-, di- or triethylene glycol (C1-C4)alkyl ethers; and mixtures thereof. The aqueous phase may also comprise sugars (such as xylitol, glucose, mannose, rhamnose and/or sorbitol), amino acids, and pyrrolidonecarboxylate derivatives or analogues such as the sodium salt of pyrrolidonecarboxylic acid (sodium PCA).

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants other than those which constitute the emulsifying system according to the invention, and mixtures thereof.

The aqueous phase generally represents from 60% to 90% by weight, relative to the total weight of the composition, preferably from 65% to 90% by weight, relative to the total weight of the composition, preferably from 70% to 85% by weight, relative to the total weight of the composition.

Additive

A composition of the invention may also comprise at least one cosmetic active agent and/or dermatological active agent.

By way of example, the active agent(s) may be chosen especially from antioxidants, sunscreens, vitamins, water-soluble or liposoluble dyes, gums, semi-crystalline polymers, antioxidants, essential oils, preserving agents, fragrances, neutralizers, moisturizers, self-tanning compounds, anti-wrinkle active agents, emollients, hydrophilic or lipophilic active agents, anti-pollution agents or free-radical scavengers, sequestrants, dermo-relaxing active agents, calmatives, agents for stimulating the synthesis of dermal or epidermal macromolecules and/or for preventing their degradation, antiglycation agents, antiirritants, desquamating agents, depigmenting, antipigmenting or pro-pigmenting agents, NO-synthase inhibitors, agents for stimulating fibroblast or keratinocyte proliferation and/or keratinocyte differentiation, agents acting on the capillary circulation, agents acting on the energy metabolism of cells, and slimming agents, and mixtures thereof.

It is a matter of routine operation for those skilled in the art to adjust the nature and the amount of the additives present in the compositions in accordance with the invention such that the desired cosmetic properties, comfort on application and stability thereof are not thereby affected.

A composition according to the invention may be intended for a cosmetic application, preferably intended for topical application.

A composition of the invention may be obtained via any preparation process known to those skilled in the art.

A subject of the invention is also a process for the cosmetic treatment of keratin materials, which consists in applying to the keratin materials a composition as defined above.

A subject of the invention is also the use of said composition in cosmetics or dermatology, and in particular for caring for, protecting and/or making up bodily or facial skin, preferably for caring for bodily or facial skin.

A composition according to the invention may especially be in the form of a composition for making up and/or caring for the skin or the lips.

A composition of the invention may be in any envisageable presentation form.

It may also be in the form of a protecting, treating or care composition for the face, for the hands, for the feet, for the major anatomical folds or for the body (for example, day cream, night cream, makeup-removing cream, antisun composition, protective or care body milk, after-سun milk, lotion, gel or foam for caring for the skin, or artificial tanning composition); a composition for making up the body or face, such as a foundation; a bath composition; a deodorizing composition comprising, for example, a bactericidal agent; an aftershave composition; a depilatory composition; a composition for countering insect stings or bites; a pain-relieving composition; or a dermatological or pharmaceutical composition for treating certain skin diseases, such as eczema, rosacea, psoriasis, lichen or severe pruritus.

A composition according to the invention can be applied by any means that allows uniform distribution and in particular using a cotton wool swab, a stick, a brush, a gauze, a spatula or a pad, or else by spraying, and can be removed by rinsing with water or using a mild detergent.

A composition according to the invention may be in paste form, in solid form, in particular a compact, pulverulent or cast form, or in a stick form.

A composition according to the invention may also be in the form of a care product, an antisun or after-sun product, a daily photoprotective care product, a body product, a foundation to be applied to the face or the neck, a concealer product, a complexion corrector, a tinted cream or a makeup base for making up the face, or a body makeup composition.

A composition according to the invention may be used for the purposes of improving the general condition of the epidermis, in particular of the skin, and especially for maintaining or restoring its physiological functions and/or its aesthetic appearance.

Thus, a composition according to the invention can advantageously be employed in order to combat ageing of the epidermis, to maintain and/or stimulate the moisturizing and/or to combat the dryness of the skin, to improve the biomechanical properties of the skin such as the tonicity of the skin, to maintain or restore the suppleness and elasticity of the skin, to improve the mineralization of the epidermis, to improve the vitality of the epidermis, to facilitate intercellular exchanges, and to combat chapping and the cracked appearance of the skin.

The invention relates in particular to a non-therapeutic cosmetic process for maintaining and/or stimulating or improving the moisturization of and/or combating the dryness of keratin materials, in particular of the skin, which consists in applying to a keratin material, preferably to the skin, in particular dry skin, one of the compositions as defined previously.

Preferably, the keratin materials, such as the skin, are human keratin materials.

The invention also relates to a non-therapeutic cosmetic process for maintaining and/or stimulating or improving the biomechanical properties of keratin materials, such as its elasticity, in particular of the skin, which consists in applying to a keratin material, preferably to the skin, one of the compositions as defined previously.

More particularly, the present invention relates to a cosmetic process for moisturizing dry skin, characterized in that one of the compositions as defined previously is applied to a dry skin.

Preferably, the non-therapeutic cosmetic treatment process according to the present invention is intended to promote the persistence of a moisturizing treatment.

In another preferred embodiment, the non-therapeutic cosmetic treatment process according to the present invention is intended for reducing and/or preventing the dehydration of keratin materials, such as the skin.

More particularly, the process of the invention, which consists in applying the compositions in the form of an oil-in-water emulsion according to the invention, especially promotes the persistence of a moisturizing treatment, and especially affords satisfactory moisturizing activity after three hours, or even after six hours, or even after eight hours, or even after 24 hours following a single application thereof to keratin materials, such as the skin.

More particularly, the process according to the invention is characterized in that said composition according to the invention is applied once or repeated one to two times per day, preferably once a day, preferably over a period of at least one week, and more particularly of at least four weeks.

The non-therapeutic cosmetic treatment process according to the present invention especially gives the keratin material, preferably the skin, long-lasting moisturization, especially after repeated application.

More particularly, the composition is applied to the keratin material, preferably the skin, i.e. onto a cutaneous region chosen from:
the hands,
the face, in particular the forehead, the cheeks or the contour of an eye (periocular), and in particular the crow's feet, the region below the eye (bag), or the eyelids,
the neck,
the feet,
the legs,
the arms and forearms.

A subject of the present invention is also the non-therapeutic cosmetic use of a composition in oil-in-water emulsion form for moisturizing and/or combating the dryness of keratin materials, such as the skin, preferably for improving the tonicity of the skin, for maintaining or restoring the suppleness and elasticity of the skin, for improving the mineralization of the epidermis, for improving the vitality of the epidermis, for facilitating intercellular exchanges, and for combating chapping and the cracked appearance of the skin, and especially for improving skin repair.

The invention will be illustrated in the non-limiting examples that follow.

Unless otherwise indicated, the amounts shown are expressed as weight percentages.

EXAMPLES

Example 1: Composition in the Form of an Oil-in-Water Emulsion According to the Invention The composition was prepared according to the following process:
Swell phase A1 at 60° C.
Add phase A2. Dissolve at 70° C.

Heat phase B1 to 70° C. Add B2 before emulsification.
Emulsify B in A.
Add the dilution phase C.
Add the gelling agent D while cooling.

| | Ingredients | Active material content/weight percentage relative to the total weight of the composition |
|---|---|---|
| A1 | Water | 35 |
| | Hydroxypropyl starch phosphate (Structure Zea ® from Akzo Nobel) | 0.88 |
| | Sodium hyaluronate | 0.1 |
| A2 | Glycerol | 7 |
| | Sodium stearoyl glutamate (Amisoft HS 11 PF ® from Ajinomoto) | 0.2 |
| | 1,3-Propanediol (Zemea Propanediol ® from DuPont Tate and Lyle Bioproducts) | 2 |
| | Pentylene glycol | 3 |
| | Phenoxyethanol | 0.4 |
| | Trisodium ethylenediamine disuccinate (Natrlquest E30 ® from Innospec Active Chemicals) | 0.09 |
| B1 | Mixture of jojoba wax, cetyl alcohol, polyglyceryl-6 distearate and polyglyceryl-3 beeswax available under the name Emulium Mellifera ® from the company Gattefossé (INCI name: Polyglyceryl-6 Distearate (and) Jojoba Esters (and) Polyglyceryl-3 Beeswax (and) Cetyl Alcohol) | 3 |
| | Behenyl alcohol (Lanette 22 ® from the company BASF) | 1 |
| | Myristyl/cetyl/stearyl myristate/palmitate/stearate mixture available under the name Crodamol MS-PA ® from the company Croda | 2 |
| | Mixture of polyglycerolated (3 mol) plant (mimosa/jojoba/sunflower) waxes sold under the name Acticire ® by the company Gattefossé | 2.5 |
| | Capryloyl salicylic acid | 0.15 |
| | Dicaprylyl ether (Cetiol OE ® from BASF) | 5 |
| | Coco-caprylate/caprate (Cetiol C 5C ® from BASF) | 2 |
| B2 | Tocopherol | 0.1 |
| C | Water | 34.32 |
| D | Fragrance | 0.3 |
| | Acid acrylamide/sodium acrylamido-2-methylpropanesulfonate copolymer as an inverse emulsion at 40% in polysorbate 80/I-C13 (available under the name Simulgel 600 ® by SEPPIC) | 0.96 |

A composition of oil-in-water emulsion type, which is the subject of the present invention, applied to the skin, forms a film on the skin which shows good resistance in a long-lasting manner, such as for at least 3 hours, and moisturizes the skin while at the same time remaining sparingly tacky and pleasant-feeling (minimized sensation of greasiness).

Example 2

Evaluation of the quality and of the occlusive nature of the film formed by compositions according to the invention, such as that of Example 1 and that of the comparative examples, was performed.

Comparative Example A Outside the Invention

| | Ingredients | AM content (weight percentage relative to the total weight of the composition) |
|---|---|---|
| A1 | Water | 35 |
| | Hydroxypropyl starch phosphate (Structure Zea ® from Akzo Nobel) | 0.88 |
| | Sodium hyaluronate | 0.1 |
| A2 | Glycerol | 7 |
| | Sodium stearoyl glutamate (Amisoft HS 11 PF ® from Ajinomoto) | 0.2 |
| | 1,3-Propanediol (Zemea Propanediol ® from DuPont Tate and Lyle Bioproducts) | 2 |
| | Pentylene glycol | 3 |
| | Phenoxyethanol | 0.4 |
| | Trisodium ethylenediamine disuccinate (Natrlquest E30 ® from Innospec Active Chemicals) | 0.09 |
| B1 | Mixture of jojoba wax, cetyl alcohol, polyglyceryl-6 distearate and polyglyceryl-3 beeswax available under the name Emulium Mellifera ® from the company Gattefossé (INCI name: Polyglyceryl-6 Distearate (and) Jojoba Esters (and) Polyglyceryl-3 Beeswax (and) Cetyl Alcohol) | 5.5 |
| | Behenyl alcohol (Lanette 22 ® from the company BASF) | 1 |
| | Myristyl/cetyl/stearyl myristate/palmitate/stearate mixture available under the name Crodamol MS-PA ® from the company Croda | 2 |
| | Capryloyl salicylic acid | 0.15 |
| | Dicaprylyl ether (Cetiol OE ® from BASF) | 5 |
| | Coco-caprylate/caprate (Cetiol C 5C ® from BASF) | 2 |
| B2 | Tocopherol | 0.1 |
| C | Water | 34.63 |
| D | Acid acrylamide/sodium acrylamido-2-methylpropanesulfonate copolymer as an inverse emulsion at 40% in polysorbate 80/I-C13 (available under the name Simulgel 600 ® by SEPPIC) | 0.96 |

Comparative Example B Outside the Invention

| | Ingredients | AM content (weight percentage relative to the total weight of the composition) |
|---|---|---|
| A1 | Water | 35 |
| | Hydroxypropyl starch phosphate (Structure Zea ® from Akzo Nobel) | 0.88 |
| | Sodium hyaluronate | 0.1 |
| A2 | Glycerol | 7 |
| | Sodium stearoyl glutamate (Amisoft HS 11 PF ® from Ajinomoto) | 0.2 |
| | 1,3-Propanediol (Zemea Propanediol ® from DuPont Tate and Lyle Bioproducts) | 2 |
| | Pentylene glycol | 3 |
| | Phenoxyethanol | 0.4 |
| | Trisodium ethylenediamine disuccinate (Natrlquest E30 ® from Innospec Active Chemicals) | 0.09 |
| B1 | Mixture of polyglycerolated (3 mol) plant (mimosa/jojoba/sunflower) waxes sold under the name Acticire ® by the company Gattefossé | 5.5 |
| | Behenyl alcohol (Lanette 22 ® from the company BASF) | 1 |
| | Myristyl/cetyl/stearyl myristate/palmitate/stearate mixture available under the name Crodamol MS-PA ® from the company Croda | 2 |
| | Capryloyl salicylic acid | 0.15 |
| | Dicaprylyl ether (Cetiol OE ® from BASF) | 5 |
| | Coco-caprylate/caprate (Cetiol C 5C ® from BASF) | 2 |
| B2 | Tocopherol | 0.1 |
| C | Water | 34.63 |
| D | Acid acrylamide/sodium acrylamido-2-methylpropanesulfonate copolymer as an inverse emulsion at 40% in polysorbate 80/I-C13 (available under the name Simulgel 600 ® by SEPPIC) | 0.96 |

The compositions of Comparative Examples A and B were prepared according to a preparation method similar to that of Example 1.

Evaluation of the Quality and Homogeneity of the Residual Film Formed after Application of a Composition The quality and homogeneity of the residual film formed by a composition according to the invention and those of the comparative examples outside the invention were studied under various temperature conditions.

This was performed by observation using a light microscope, with the protocol as described below:
  Deposition of a 50 μm film using an automatic spreader on a PET film
  Deposition of the film in an air-conditioned room for 3 hours (4° C., 40° C., room temperature RT) or for 1 hour 30 minutes at 4° C. and then 1 hour 30 minutes at 40° C., and 1 hour 30 minutes at 40° C. and then 1 hour 30 minutes at 4° C.
  Observation of the film using a light microscope and taking of photographs The films formed with the compositions of Comparative Examples A and B outside the invention are no longer homogeneous (presence of cracking) and are of poor quality from 1 hour 30 minutes at 40° C.

It was found, surprisingly, that the film formed by the composition of Example 1 according to the invention is of good quality and homogeneous, and that this quality and homogeneity are conserved over time and at elevated temperature; the film is of very good quality and homogeneous (no presence of cracking), whether after 3 hours at 4° C. and at room temperature, or after 3 hours at 40° C.

Surprisingly, the film formed with the composition of Example 1 according to the invention also remains of good quality and homogeneous after 8 hours at 4° C. or at room temperature.

Evaluation of the Occlusive Properties of a Film Formed with the Composition of Example 1 According to the Invention The efficacy of a film formed with a composition, especially in cream form, for reducing water loss, when it is applied to keratin materials such as the skin, was evaluated quantitatively according to the method described by Sparr et al., 2012. This efficacy is expressed by calculating the specific resistance (SR, $m \cdot h \cdot g^{-1}$), which is explained in the article *Controlling the hydration of the skin through the*

*application of occluding barrier creams* (Emma Sparr et al.; 2012; rsif.royalsocietypublishing.org).

It was shown (Sparr et al. (2012)) how the environmental conditions could be modified by applying a protective cream forming a film with high resistance to water transport, especially via a quantitative mathematical model which predicts the moisturization and the transportation of water into the stratum corneum covered with such a cream film, and an experimental method for measuring the specific resistance to water transport of the films formed with these protective creams was developed.

This characterization method made it possible, firstly, to demonstrate that water-in-oil inverse emulsions usually have a higher SR than the direct emulsions of the prior art (400>SR>200 m·h·g$^{-1}$ versus 1>SR>150 m·h·g$^{-1}$).

For the purposes of the present invention, it is considered that compositions in oil-in-water emulsion form have a good film-forming effect, i.e. good moisturizing properties, for an SR (specific resistance) of greater than or equal to 100 m·h·g$^{-1}$.

The specific resistance values presented below are the means of measurements repeated twice or three times.

The thickness of the film formed with a composition according to the invention was also evaluated.

| Compositions tested | Composition 1 according to the invention |
|---|---|
| Dry film thickness (μm) | 42 |
| Specific resistance (m · h · g$^{-1}$) | 148 |

It was found, surprisingly, that the particular choice of a nonionic surfactant system of ester type combined with a particular wax according to the invention makes it possible to obtain a thin film while at the same time allowing a good specific resistance of the film formed from the composition in oil-in-water emulsion form, but which is not too high, and especially is lower than that of an inverse emulsion and thus allows a less occlusive film.

Example 3

Evaluation of the Biomechanical Properties of the Skin, Such as the Elasticity Under Elevated Humidity and Temperature Conditions after Application of a Composition According to the Invention A composition according to that of Example 1 of the invention was applied to half-faces of 12 individuals, in an amount of 2 mg/cm$^2$. The individuals then remained in a steam bath for 30 minutes (conditions: temperature of 29° C. and 70% relative humidity RH).

The elasticity of the facial skin was observed after the time in the steam bath.

It was found that the composition according to the invention makes it possible to improve the elasticity of the skin, and does so after variable temperature and humidity conditions of the environment.

The invention claimed is:
1. A composition of oil-in-water emulsion type comprising:
   at least one polyol in a content ranging from 7% to 25% by weight relative to the total weight of the composition;
   water in a content ranging from 60% to 90% by weight relative to the total weight of the composition;
   at least two nonionic surfactants that are different from each other, chosen from a nonionic surfactant of ester type comprising
   i) at least one unsaturated ester of formula (A):

$$R^1-C(O)-O-R^2 \tag{A}$$

in which:
   $R^1$ and $R^2$ represent, respectively, a C18 to C44 fatty chain, and at least $R^1$ or $R^2$ is monounsaturated;
   ii) at least one polyglycerol diester of formula (B):

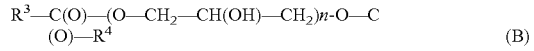

$$R^3-C(O)-(O-CH_2-CH(OH)-CH_2)n\text{-}O-C(O)-R^4 \tag{B}$$

in which:
   n=2 to 6
   $R^3$ and $R^4$ represent, respectively, a saturated, linear or branched C18 to C44 fatty chain, and
      at least one other nonionic surfactant chosen from C10-C30 fatty alcohols;
   at least one wax being a mixture of polyglycerolated mimosa, jojoba and sunflower plant waxes;
   and the mass ratio [total amount of said nonionic surfactant(s) of ester type]/[total amount of said wax] ranges from 0.8 to 2.
2. The composition according to claim 1, characterized in that said polyol(s) are chosen from linear polyols comprising at least two —OH functions and comprising from 3 to 8 carbon atoms.
3. The composition according to claim 1, which comprises at least one anionic surfactant.
4. The composition according to claim 1, wherein
   the nonionic surfactant of ester type comprises at least one monounsaturated ester of formula (A) in which $R^1$ and $R^2$ represent, respectively, a C18 to C30 fatty chain; at least one polyglycerol diester of formula (B) in which $R^3-C(O)-$ and $R^4$ each represent a linear or branched, saturated C20-C34 fatty chain; and cetyl alcohol.
5. The composition according to claim 4, characterized in that it also comprises a diester of a C14-C22 fatty acid with a polyglycerol and/or a fatty alcohol comprising from 10 to 30 carbon atoms.
6. The composition according to claim 4, wherein the nonionic surfactant of ester type is a mixture of polyglyceryl-6 distearate, jojoba esters, polyglyceryl-3 beeswax and cetyl alcohol.
7. The composition according to claim 1, wherein the nonionic surfactant(s) of ester type are present in a content of from 1% to 6% by weight relative to the total weight of the composition.
8. The composition according to claim 3, wherein the at least one anionic surfactant is chosen from triethanolamine cocoyl glutamate, triethanolamine lauroyl glutamate, monocetyl phosphate, the combination of the monosodium salt of N-stearoyl-L-glutamic acid, and mixtures thereof.
9. The composition according to claim 1, which also comprises at least one oil of formula $R_6COOR_5$, in which $R_6$ represents a linear or branched fatty acid residue comprising from 1 to 40 carbon atoms, and $R_5$ represents a hydrocarbon-based chain, containing from 1 to 40 carbon atoms, provided that $R_6+R_5\geq 10$.
10. The composition according to claim 9, wherein the at least one oil of formula $R_6COOR_5$ is chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

11. The composition according to claim 1, wherein the fatty alcohol(s) comprise from 16 to 22 carbon atoms.

12. The composition according to claim 1, wherein the fatty alcohol(s) are present in a total content of from 0.5% to 15% by weight relative to the total weight of the composition.

13. The composition according to claim 1, which comprises at least one gelling agent.

14. The composition according to claim 1, which comprises at least one gelling agent chosen from crosslinked anionic copolymers of acrylamide and of 2-acrylamido-2-methylpropanesulfonic acid.

15. The composition according to claim 1, wherein said composition is a stable cosmetic composition.

16. A non-therapeutic cosmetic process for making up and/or caring for keratin materials, comprising at least the application to said materials of a composition as defined according to claim 1.

17. The non-therapeutic cosmetic process according to claim 16, characterized in that it is intended for maintaining and/or improving the moisturization of keratin materials, and/or for improving the biomechanical properties of these said keratin materials.

18. The composition according to claim 1, which comprises at least one anionic surfactant selected from the group of glutamic acid salts, salts of esters of phosphoric acid and of fatty alcohol, and alkyl sulfates, and mixtures thereof.

19. The composition according to claim 1, wherein the nonionic surfactant(s) of ester type are present in a content of from 1% to 6% by weight relative to the total weight of the composition; the at least one wax is present in a content of from 0.5% to 5% by weight relative to the total weight of the composition, and the mass ratio [total amount of said nonionic surfactant(s) of ester type]/[total amount of said wax] ranges from 1 to 1.5.

20. The composition according to claim 1, which is a stable cosmetic composition wherein the fatty alcohol(s) are present in a total content of from 0.5% to 15% by weight relative to the total weight of the composition; the nonionic surfactant(s) of ester type are present in a content of from 1% to 6% by weight relative to the total weight of the composition; the at least one wax is present in a content of from 0.5% to 5% by weight relative to the total weight of the composition, and the mass ratio [total amount of said nonionic surfactant(s) of ester type]/[total amount of said wax] ranges from 1 to 1.5.

* * * * *